(12) United States Patent
Clermont et al.

(10) Patent No.: US 8,178,340 B2
(45) Date of Patent: May 15, 2012

(54) **HUMAN SPECIFIC *ESCHERICHIA COLI* STRAINS**

(75) Inventors: Olivier Clermont, Romainville (FR); Erick Denamur, Paris (FR); Tony Le Gall, Brest (FR); Olivier Tenaillon, Chatenay Malabry (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 0 days.

(21) Appl. No.: 12/673,614

(22) PCT Filed: Aug. 13, 2008

(86) PCT No.: PCT/EP2008/060648
§ 371 (c)(1),
(2), (4) Date: Feb. 16, 2010

(87) PCT Pub. No.: WO2009/021977
PCT Pub. Date: Feb. 19, 2009

(65) Prior Publication Data
US 2011/0008449 A1    Jan. 13, 2011

(30) Foreign Application Priority Data

Aug. 16, 2007    (EP) ..................................... 07301308

(51) Int. Cl.
*C12N 1/20*    (2006.01)

(52) U.S. Cl. ................. 435/252.33; 435/243; 435/252.1; 424/241.1

(58) Field of Classification Search ........................ None
See application file for complete search history.

(56) References Cited

OTHER PUBLICATIONS

Clermont et al., Environmental Microbiology, 10(4):1000-1006 (2008).
Escobar-Paramo et al., Mol. Biol. Evol., 21(6):1085-1094 (2004).
Johnson et al., J. Infect. Dis., 194:1141-1150 (2006).
Le Gall et al., Mol. Biol. Evol., 24(11):2373-2384 (2007).

*Primary Examiner* — Jennifer Graser
(74) *Attorney, Agent, or Firm* — McAndrews, Held & Malloy Ltd.

(57) ABSTRACT

The present invention relates to human specific *Escherichia coli* strains.

4 Claims, 2 Drawing Sheets

A

B

HUMAN SPECIFIC ESCHERICHIA COLI STRAINS

Figure 1:
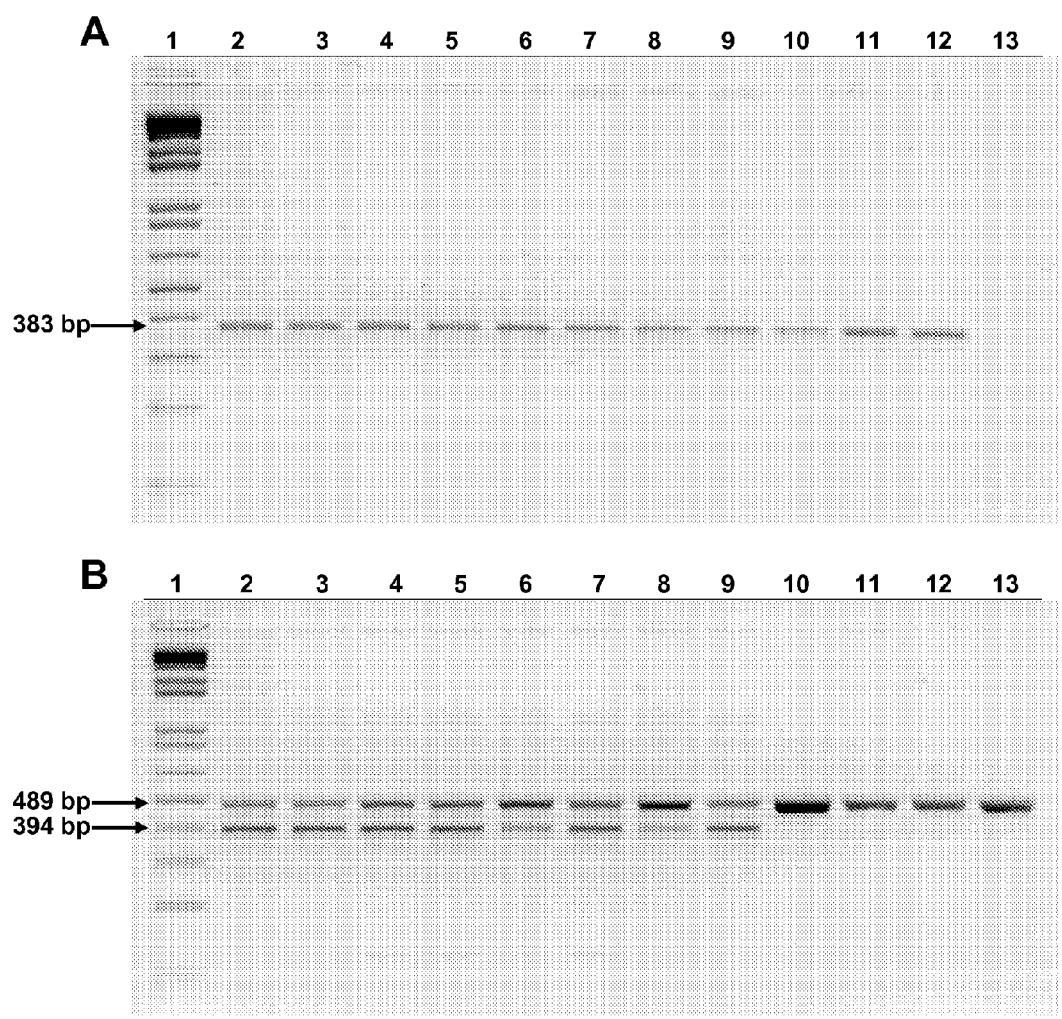

The present application is filed pursuant to 35 U.S.C. 371 as a U.S. National Phase application of International Patent Application No. PCT/EP08/60648, which was filed Aug. 13, 2008, claiming the benefit of priority to European Patent Application No. 07301308.8, which was filed on Aug. 16, 2007. The entire text of the aforementioned applications is incorporated herein by reference in its entirety.

FIELD OF THE INVENTION

The present invention relates to *Escherichia coli* strains

BACKGROUND OF THE INVENTION

*Escherichia coli* is a widespread commensal of the lower intestinal tract of humans and other vertebrates that occasionally causes intestinal and extra-intestinal diseases (Donnenberg 2002). *E. coli* is used as a probiotic but the currently used probiotic strains, Nissle O6 strain (Mutaflor®) isolated in 1917 from the faeces of a healthy soldier (Sun et al., 2005) and the A0 34/36 O83 strain isolated from porcine faeces (Hejnova, et al., 2005), are highly virulent in a mouse model of extra-intestinal virulence (Johnson et al., 2006).

*E. coli* colonizes a wide variety of hosts with very diverse gut morphologies and digestive physiologies. *E. coli* also exhibits quite substantial genetic structure, with most commensal isolates belonging to one of four genetic groups (A, B1, D and B2) (Herzer et al., 1990). The great majority of *E. coli* strains belonging to genetic group B2 are highly virulent in a mouse model (Johnson et al., 2006).

Epidemiological studies have only demonstrated weak associations between host species and the prevalence of strains of the four phylogenetic groups (Gordon and Cowling 2003; Escobar-Páramo et al., 2006). Although the frequency of the four genetic groups varies to some degree with the diet or body mass of the host from which it was isolated, other factors such as climate, the year of sampling, or the domestication status of the animals sampled (wild versus domesticated) also shape the global genetic structure of *E. coli*. To date, no strong association between a particular clone and a given host species has been found, except perhaps for a hly B1 clone that appears to be restricted to animals (Gordon and Cowling 2003; Escobar-Páramo et al., 2004b; Escobar-Páramo et al., 2006).

*E. coli* has been used for many years to assess water quality and to determine the source of any faecal pollution that might occur in a water body (Scott et al., 2002). However, the use of *E. coli* in these efforts has been hampered by the apparent lack of any extensive host-specificity in *E. coli* (Gordon, 2001) and by the ability of many *E. coli* strains to undergo significant cell division in the external environment (Barnes and Gordon, 2004; Power et al., 2005). The usefulness of the microbial indicators as tool risk assessment can be significantly enhanced by the identification of a human specific clone.

SUMMARY OF THE INVENTION

The invention relates to human specific *Escherichia coli* strains which are avirulent and uses thereof.

DETAILED DESCRIPTION OF THE INVENTION

The present invention relates to strains of *Escherichia coli* of O81 serotype belonging to the B2 subgroup VIII.

These strains are human specific and avirulent.

The serotype of the strains according to the invention may be determined via traditional serology (Dr Chobi Deb Roy, *E. coli* reference center, Pennsylvania State University, USA) or O81 specific primer pair may be used. For example an O81 specific forward primer (rfbO81bis.r: 5'-GAGCAG-TATATATTACTGGTG-3' (SEQ ID NO: 10)), together with a reverse primer (gndbis.f: 5'-ATACCGACGACGC-CGATCTG-3' (SEQ ID NO: 11)) can be used).

Primers to confirm that a strain is a member of the B2 clonal group VIII may be used. For example specific primers for the trpA gene may be used, in particular the forward primer (trpAVIII.f: 5'-GCGCAAAGAAGGCGCATTCA-3' (SEQ ID NO: 8)) which is specific to B2 VIII strains together with a non-specific trpA reverse primer (trpA2.r: 5'-GCAACGCGGCCTGGCGGAAG-3' (SEQ ID NO: 9)).

By "avirulent" it is meant a strain which does not cause disease in human subjects. Avirulent strains do not present extraintestinal nor intestinal virulence in human subjects.

The extraintestinal virulence of the strain may be assessed by using a mouse model of systemic infection, such as that described in Picard et al. (1999) or in Johnson et al. (2006). Typically, a strain that is avirulent in a mouse model of systemic infection is not responsible for extra-intestinal infection in human.

The intestinal virulence of the strain is directly related to the enteroaggregative phenotype of said strain. This phenotype, also called "aggregative adherence" can be tested in a cellular model of adherence on Hep-2 cells (see Nataro et al., 1998) and is due to the presence of the AAF-II gene present on a plasmid.

A strain according to the invention may be isolated and purified from human gastrointestinal tract.

In a preferred embodiment, a strain according to the invention comprises six sequences with at least 99% identity with SEQ ID NO: 1, SEQ ID NO: 2, SEQ ID NO: 3, SEQ ID NO: 4, SEQ ID NO: 5 and SEQ ID NO: 6 respectively.

Typically a strain according to the invention comprises six sequences with at least 99.5% identity, for example at least 99.9% identity, with SEQ ID NO: 1, SEQ ID NO: 2, SEQ ID NO: 3, SEQ ID NO: 4, SEQ ID NO: 5 and SEQ ID NO: 6 respectively.

SEQ ID NO: 1 to 6 correspond respectively to the sequences of the following genes: trpA, trpB, pabB, putP, icd, polB.

The percentage of identity may be determined by using algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988), the local homology algorithm of Smith et al. (1981), the homology alignment algorithm of Needleman and Wunsch (1970), the search-for-similarity-method of Pearson and Lipman (1988), the algorithm of Karlin and Altschul (1990) modified as in Karlin and Altschul (1993). Computer implementations of these mathematical algorithms can be utilized for comparison of sequences to determine sequence identity. Such implementations include, but are not limited to: CLUSTAL in the PC/Gene program (available from Intelligenetics, Mountain View. Calif.); the ALIGN program (Version 2.0) and GAP, BESTFIT. BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

A preferred embodiment of the invention relates to a strain of *Escherichia coli* called ED1a deposited at the COLLECTION NATIONALE DE CULTURES DE MICROORGANISMES (CNCM, Institut Pasteur, 25 rue due Docteur Roux, 75724 Paris CEDEX 15-France) on Mar. 29, 2007 in accordance with the terms of the Budapest Treating under the accession number CNCMI-3734.

The genome of ED1a has been fully sequenced. The sequence of the genome of ED1a is set forth in SEQ ID NO: 7.

A strain according to the invention may be used as a probiotic. Typically the strains according to the invention may have the same type of applications as the Nissle O6 strain or the A0 34/86 O83 strain.

Typically a strain according to the invention may be used for the treatment and/or prevention of a disease in a subject in need thereof.

In a preferred embodiment said disease may be selected from the group consisting of bowel diseases such as ulcerative colitis, Crohn's disease, inflammatory bowel diseases, pouchitis, collagenous colitis, irritable bowel syndrome, chronic constipation, chronic diarrhea, antibiotic-associated pseudomembranous colitis, diverticular disease of the colon, intestinally caused halitosis, polymorphous light eruption, non-ulcer dyspepsia, food intolerance, food malabsorptions, and mycoses of the orogastrointestinal tract.

In a preferred embodiment said disease is an extra-intestinal *E. coli* infection.

An embodiment of the invention relates to a method of treatment and/or prevention of a disease, comprising administering in a subject in need thereof a therapeutically effective amount of a strain according to invention.

In the context of the invention, the term "treating" or "treatment", as used herein, means reversing, alleviating, inhibiting the progress of, or preventing the disorder or condition to which such term applies, or reversing, alleviating, inhibiting the progress of, or preventing one or more symptoms of such a disorder or condition.

By a "therapeutically effective amount" of a strain according to the invention is meant a sufficient amount of the strain to treat said disease, at a reasonable benefit/risk ratio applicable to any medical treatment. It will be understood, however, that the total daily usage of the strain of the present invention will be decided by the attending physician within the scope of sound medical judgment. The specific therapeutically effective dose level for any particular subject will depend upon a variety of factors including the disease being treated and the severity of the disease, the age, body weight, general health, sex and diet of the subject, the time of administration, route of administration, the duration of the treatment; drugs used in combination or coincidental with the strain employed, and like factors well known in the medical arts.

Typically strains according to the invention may be lyophilized and supplied to a subject in need thereof in enteric-coated formulations, such as capsules or tablets. An embodiment of the invention relates to an enteric-coated formulation comprising lyophilized strain according to the invention. Typically an enteric coated formulation may contain between $0.1 \times 10^9$ to $30 \times 10^9$ bacteria according to the invention.

A strain according to the invention may be genetically modified and thus contain one or more heterologous nucleotide sequences and may be used for example as a bacterial vector. Typically a strain according to the invention may be used for genetic vaccination or gene therapy. Non pathogenic *E. coli* have already been used for these purposes (see for review Vassaux et al. 2006).

A strain according to the invention may also be used as a biosensor (Harms et al., 2006), in particular for the detection of colorectal cancer. Cancerous cells express on their surface a number of proteins which may, when detected, be helpful in diagnosing a cancer. Typically, a strain according to the invention may be genetically modified in order to express a reporter protein. This engineered strain can then enable the detection of cancerous proteins by emitting a physiological response which can be quantified in the faeces after administration to a patient.

An embodiment of the invention relates to a method of diagnosis of a colorectal cancer, comprising administering in a subject in need thereof a genetically modified strain according to invention.

A further embodiment of the invention relates to a method for detecting a water contamination by human faeces comprising the detection of an *E. coli* strain according to the invention.

In a preferred embodiment, said detection involves a PCR step using primers which are specific to an *E. coli* strain according to the invention or using a nucleotide probe specific to an *E. coli* strain according to the invention.

In a preferred embodiment, said detection involves the use of a specific antibody against an *E. coli* strain according to the invention.

In the following, the invention will be illustrated by means of the following examples as well as the figures.

FIGURE LEGENDS

FIG. 1: Allele specific PCR of (A) the 5' portion of the rfb cluster amplifying the O81 type and (B) the trpA gene amplifying the B2 subgroup VIII. In B, the 489 bp fragment present in all tested strains corresponds to a control of amplification of trpA gene. Lane 1: molecular weight marker (1 Kb Plus DNA ladder, Invitrogen, Cergy Pontoise, France), lane 2: ED1a, lane 3: VDG427, lane 4: Ben4d, lane 5: Ben27a, lane 6: colF12g, lane 7: col 13c: lane 8: 381A, lane 9: IAI48, lane 10: O81 strain of the B1 phylogenetic group isolated from a septicaemic chicken, lane 11: O81 strain of the A phylogenetic group isolated from cotton rat faeces, line 12: O81 strain of the B2 phylogenetic group isolated from human faeces in commensal conditions, line 13: CFT073 strain of O6 type belonging to the B2 phylogenetic group. Strains from lines 2 to 9 belong to the O81 subgroup VIII clone.

Figure 2:
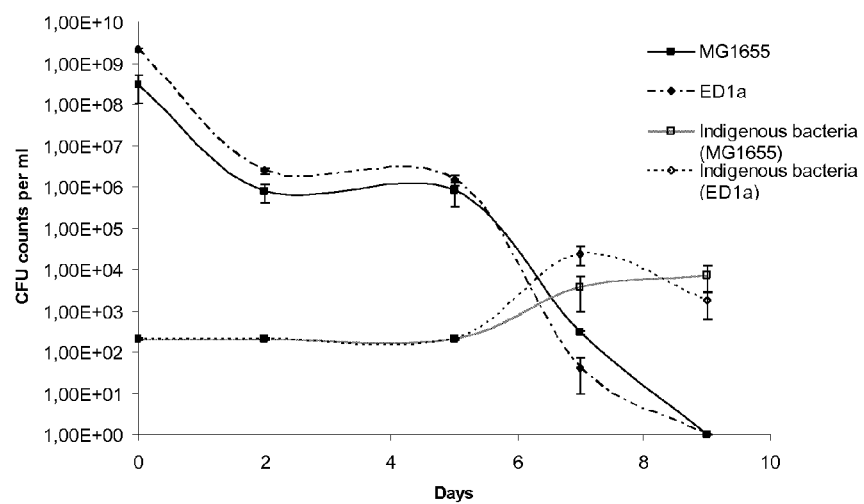
Figure 2:
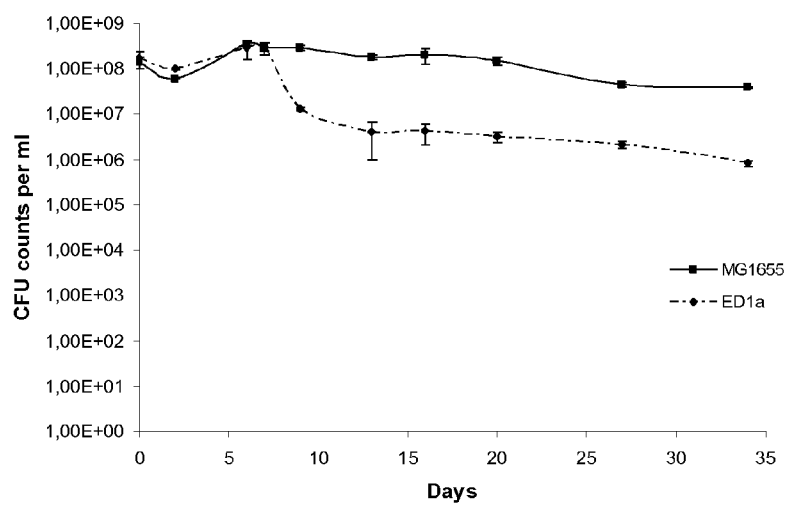

FIG. 2: Decline of K12-MG1655 and ED1a *E. coli* cells in (A) non sterile and (B) sterile water of the Saint Martin canal in Paris at 20° C. Indigenous bacteria counts are indicated in the non sterile experiment.

EXAMPLES

Experimental Procedures

Bacterial Strains

Several previously published collections were studied. A collection of 293 isolates representing all the B2 strains among 1520 isolates from the faeces of 152 humans (10 strains per individual) (Escobar-Páramo et al., 2004b). These strains originated from Benin (68 isolates from 24 subjects), Colombia (81 isolates from 18 subjects) and France (144 isolates from 25 subjects) and were obtained post 2000. Twenty five human faecal B2 isolates from 25 subjects originating from Europe (France, Sweden, Croatia), Africa (Mali) and America (USA) and sampled in the 1980's (Ochman and Selander, 1984; Duriez et al., 2001) were also studied. A collection of 378 faecal isolates (310 isolates from 87 mammals, 68 isolates from 23 birds) consisting all the B2 strains among 1930 isolates from the faeces of 405 animals (one to 10 strains per individual). These strains were sampled between 1980 and 2000 in France, Africa (Ethiopia, Cameroon, Gabon) and the Americas (French Caribbean Islands, Venezuela, U.S.A) from domestic or wild (Escobar-Páramo et al., 2006) or zoo (Ochman and Selander, 1984) animals. A collection of 55 pathogenic B2 strains from humans (one strain per patient) encompassing enteropathogenic, enteroaggregative, diffusely adhering and extra-intestinal pathovars (Ochman and Selander, 1984; Picard et al., 1999; Escobar-Páramo et al., 2004a). These strains originated from Europe (France, Sweden), America (Brazil, U.S.A.) and Africa (Central African Republic) and were collected between 1980 and 2000. The collection of strains isolated from humans living in the Canberra region of Australia was acquired by isolating a single colony from the faeces or an extra-intestinal body site of each person sampled (Gordon et al. 2005; Gordon and O'Brien, 2006). A total of 120 B2 faecal isolates and 230 B2 strains taken from extra-intestinal body sites were examined for this study. The Gordon collection of strains from native wild Australian vertebrates was acquired by selecting a single isolate from each faecal sample and a single faecal sample was taken from each host individual (Gordon and Cowling, 2003). The numbers of Australian B2 strains examined were mammals (n=234), birds (n=30), and reptiles (n=4). A collection described by Souza et al. (1999) consisting of 258 *E. coli* faecal isolates from animals was analysed. For the Souza collection a single isolate per host was taken from faecal material of the following host types; mammals (n=197), birds (n=51) and reptiles (n=10) living primarily in Central and South America. Lastly, 15 O81 *E. coli* strains isolated from the hearts of 15 chickens suffering from septicaemia in Spain during the 1990's (Blanco et al., 1997) were also studied.

PCR Screening of O81 and B2 Subgroup VIII Strains

The serotype of the B2 clonal group VIII strain ED1a was determined via traditional serology (Dr Chobi Deb Roy, *E. coli* reference center, Pennsylvania State University, USA). To design an O81 specific primer pair the approach described by Clermont et al. (2007) was used. First, the 5' extremity of the rfb cluster from ED1a was sequenced and using this sequence data an O81 specific primer was designed (rfbO81bis.r: 5'-GAGCAGTATATATTACTGGTG-3' (SEQ ID NO: 10)), this primer together with (gndbis.f: 5'-ATAC-CGACGACGCCGATCTG-3' (SEQ ID NO: 11)) yields a 383 bp fragment (FIG. 1A).

Primers to confirm that a strain was a member of the B2 clonal group VIII were designed for the trpA gene. The forward primer (trpAVIII.f: 5'-GCGCAAAGAAGGCGCAT-TCA-3' (SEQ ID NO: 8)) is specific to B2 VIII strains and together with a non-specific trpA reverse primer (trpA2.r: 5'-GCAACGCGGCCTGGCGGAAG-3' (SEQ ID NO: 9)) produces a 394 bp fragment. The universal forward primer targeting the 3' portion of trpB (trpBA.f: 5'-CGGCGATAAA-GACATCTTCA-3' (SEQ ID NO: 12)) which, together with SEQ ID NO: 9, yields a 489 bp product from all *E. coli* strains and was included in the reaction as a positive control (FIG. 1B).

PCR reactions were carried out in a 20-µl volume and contained 2 µl of 10× buffer (supplied with Taq polymerase), 20 pmol of each primer, 2 µM each dNTP, 1 U of Taq polymerase (Ozyme, St Quentin en Yvelines, France), and 3 µl of bacterial lysate. PCR reactions were performed with an Eppendorf Mastercycler with MicroAm tubes using the following amplification conditions: 4 min at 94° C., 30 cycles of 5 sec at 94° C. and 10 sec at 59° C., with a final extension step of 5 min at 72° C. PCR products were loaded on 2% agarose gels containing SYBR® Safe DNA gel strain (Invitrogen, Cergy Pontoise, France) and visualized and photographed under UV light.

MLST Analysis

The phylogenetic relationships among the strains were inferred using nucleotide sequence data from 6 essential genes [trpA, trpB, pabB, putP, icd, and polB (Gerdes et al. 2003)] which are thought to experience little recombination and produce a strong phylogenetic signal (Escobar-Páramo et al. 2004c). Sequence data for the 6 genes was concatenated and aligned.

Virulence Gene Detection

The following 19 genes, usually considered as "virulence determinants" and involved in capsule synthesis (neuC), adhesion (papC, papG, sfa/foc), toxin production (hly, cnf1), iron metabolism (iron, ireA, aer, aer, fyuA, irp2, iha) and other traits (hra, sat, usp, ompT, ibeA, malX, traT), were detected by using established simplex or multiplex PCR assays (Johnson et al., 2006).

Survival of *E. coli* Strains in Water

The river water used was obtained from the Saint Martin canal in Paris at a site about 1 km upstream from the Seine. For the sterile water studies, the water was autoclaved for 45 min. One hundred-milliliter aliquots of water were placed into 250-milliliter Erlenmeyer flasks capped with paper covers. After inoculation, the flasks were incubated at 20° C. under a 12:12 light:dark cycle. Indigenous bacteria were present at a level of about $2 \times 10^2$ CFU/ml of river water. Fresh cultures of the strains K12-MG1655 and ED1a that had been grown for 14 h in 10 ml of Luria-Bertani (LB) medium, were washed with sterile 0.9% saline, centrifuged, re-suspended in 1 ml and added to the water. Samples for counting were removed directly from the water, diluted and plated on Drigalsky and LB (non-sterile water) or LB (sterile water) media. In the non-sterile water experiment, the differentiation between indigenous and inoculated bacteria was based on colony morphology and O81 PCR assay. All experiments were done in duplicate.

Mouse Lethality Assay

A mouse model of systemic infection was used to assess the intrinsic virulence of the O81 strains (Picard et al., 1999). For each strain, 10 outbred female Swiss OF1 mice (3-4 weeks old, 14-16 gm) were challenged subcutaneously in the abdomen with a standardized bacterial inoculum ($10^9$ cfu/ml of log-phase bacteria in 0.2 ml Ringer solution). Mortality was assessed over 7 days post-challenge. The urosepsis strains CFT073 was used as a positive control and the faecal-derived strain K12-MG1655 as a negative control. In this model system, lethality is a rather clear-cut parameter and strains were usually classified as non killer (strains killing <2 mice out of 10) or killer (strains killing >8 mice) (Johnson et al., 2006).

Enteroaggregation Assay

Aggregative adherence is tested in a cellular model on Hep-2 cells, as described in Nataro et al., 1998.

Results

Global Distribution of the B2 VIII/O81 Clone

A total of 1369 strains belonging to phylogenetic group B2 representing 438 faecal and 285 clinical isolates from humans, as well as 646 isolates from the faeces of wild, domestic and zoo animals were screened using the O81 specific primer. An additional 258 isolates from non-domestic animal faeces, whose phylogenetic group membership had not been determined, were also screened, as well as 15 O81 strains of undetermined phylogenetic group from septicaemic chickens. All O81 positive strains were screened using the B2 clonal group VIII specific primers and, if unknown, their phylogenetic group membership was determined.

Despite surveying strains from over sixty animal species living on four continents, none of the animal isolates were found to possess the O81 locus and to be members of B2 clonal group VIII. By contrast, 64 members of the B2 VIII/O81 clone were detected among the human isolates (FIG. 1). Two of the B2 VIII/O81 strains were clinical isolates; one strain was responsible for a urinary tract infection, IAI48 (Picard et al., 1999) and the other was an enteroaggregative strain responsible for a case of diarrhoea, 381A (Escobar-Páramo et al., 2004a). B2 VIII/O81 strains were isolated from humans living in Africa, the Americas, and Europe, but not from people living in Australia.

Seven B2 strains from both non-human vertebrates and humans yielded an O81 PCR product but were not members of the B2 clonal group VIII, indicating that the O81 serotype can be found outside the B2 clonal group VIII. Further, 18 O81 positive strains belonging to phylogenetic groups A and B1 were detected [3 strains (1 group A and 2 group B1) from mammals living in the Americas, as well as 15 B1 strains from chickens sampled in Spain]. All of the O81 strains that were not members of the B2 clonal group VIII exhibited a polymorphic pattern of virulence determinants, that was, in every case, distinct from the B2 VIII/O81 clone (data not shown).

To assess the degree of sequence type diversity among the B2 VIII/O81 strains, we choose 6 isolates from different hosts and geographical regions, as well as the two disease causing isolates (Table 1) for further characterisation. We first performed MLST by sequencing 6 essential genes (6021 bp) in these strains. The sequences were all identical except for one strain (BEN4d) that has a synonymous polymorphism in the putP gene.

We also performed an in silico search for strains of the B2 VIII/O81 clone in the Max Planck Institute MLST database (http://web.mpiib-berlin.mpg.de/mlst/dbs/Ecoli). This database contained, at the time it was searched, data for 1404 disease and faecal isolates largely recovered from humans and domesticated animals. To accomplish this search, the allele sequence for each of the seven genes used in this MLST scheme (adk, fumC, gyrB, icd, mdh, recA and purA) was determined for the B2 VIII/O81 strain ED1a. Only one strain (M716, ST 452), an isolate from an Australian mammal, matched the profile of ED 1a. However, this isolate does not yield an O81 PCR product, and M716 differs from ED1a at 7 bases over the 727 nucleotides of trpA locus, including the allele specific site of the trpAVIII.f primer, as well as in its virulence profile.

We also tested the strains for the presence of AAF-II gene, responsible for the aggregative adherence phenotype. This gene was only present in the 381A strain.

Virulence Characteristics of B2 VIII/O81 Strains

The 8 B2 VIII/O81 strains were tested in an experimental mouse model of extra-intestinal virulence. Whereas most B2 strains exhibit a high virulence in such a model (Johnson et al., 2006), none of the tested strains had any virulence in this extra-intestinal model. We then screened the isolates for the presence of 19 putative virulence determinants associated with extra-intestinal disease. All the strains exhibited a similar virulence gene profile (Table 1). The iron metabolism genes ireA, aer and iha were present in all strains. However, the genes fyuA, and irp2, which are markers for the high pathogenicity island, were absent from some strains.

Intestinal virulence is tested in the cellular model for aggregative adherence. The 381A strain is found to be enteroaggregative in this model.

TABLE 1

Principal characteristics of the 8 representative human O81 B2 subgroup VIII clone strains studied

| Strain | Host origin | Condition of isolation | neuC | papC | papG | sfa/foc | hly | cnf1 | iroN | ireA |
|---|---|---|---|---|---|---|---|---|---|---|
| ED1a | France | Com[a] | − | − | − | − | − | − | − | + |
| VDG427 | France | Com | − | − | − | − | − | − | − | + |
| Ben4d | Benin | Com | − | − | − | − | − | − | − | + |
| Ben27a | Benin | Com | − | − | − | − | − | − | − | + |
| colF12g | Colombia | Com | − | − | − | − | − | − | − | + |
| colH13c | Colombia | Com | − | − | − | − | − | − | − | + |
| 381A | Central African Republic | Diarrhea (EAEC[b]) | − | − | − | − | − | − | − | + |
| IAI48 | France | UTI[c] | − | − | − | − | − | − | − | + |

| Strain | aer | fyuA | irp2 | iha | hra | sat | usp | ompT | ibeA | malX | traT |
|---|---|---|---|---|---|---|---|---|---|---|---|
| ED1a | + | + | + | + | − | − | + | + | − | + | − |
| VDG427 | + | − | − | + | − | − | + | + | − | + | − |
| Ben4d | + | − | − | + | − | − | + | + | − | + | − |
| Ben27a | + | + | + | + | − | − | + | + | − | + | − |
| colF12g | + | + | + | + | − | − | + | + | − | + | − |
| colH13c | + | − | − | + | − | − | + | + | − | + | − |
| 381A | + | − | − | + | − | − | + | + | − | + | − |
| IAI48 | + | − | − | + | − | − | + | + | − | + | − |

[a]Commensal
[b]Entero aggregative E. coli
[c]Urinary tract infection

Fine Scale Analysis of the Epidemiologic Data

In a sample of faecal isolates collected post 2000 from 152 people living in Colombia, Benin, and France, and considering one randomly selected isolate per individual, the B2 VIII/O81 clone represented 4% (3 to 7% according to the population) of all isolates and 18% (11 to 28% according to the population) of the B2 strains recovered. By contrast, in a sample of faecal isolates collected in the 1980's from 193 people living in the U.S.A. Mali, Croatia, France and Sweden, the B2 VIII/O81 clone represented only 0.4% of all isolates tested and 4% of the B2 strains. This result suggests that the VIII/O81 clone has increased its representation in human faeces 10-fold in the past twenty years.

To determine if the B2 VIII/O81 clone persists at a high frequency within a host we analysed the dataset cited above, but used all 10 isolates taken from each of the 152 subjects. O81 was detected in 12 of the 152 hosts and, in 42% of these people, the O81 clone represented at least 80% of the *E. coli* isolates recovered from that host. By contrast a non-VIII/O81 B2 strain was detected in 58 hosts, but in these cases the B2 strain represented >80% of the *E. coli* in that host only 17% of the time. Put differently, 77% of the O81 strains detected were found in hosts in which they were the majority clone (>80%), whereas only 37% of non-O81 strains were found in a situation where they represented the majority (>80%) of the *E. coli* in a host. This outcome suggests that the B2 VIII/O81 clone is able to achieve numerical dominance in a human more often than other group B2 strains.

Analysis of Strains from Septicaemic Patients 161 strains obtained from *E. coli* septicaemia episodes were collected and studied (Jauréguy et al., 2007). Eighty strains belonged to the B2 phylogenetic group, but none of them to the B2 VIII/O81 clone.

Moreover, analysis of 1029 *E. coli* septicaemia strains collected in 2005 in the clinical protocol Colibafi (http://www.colibafi.net) shows an absence of strains belonging to the B2 VIII/O81 clone among the 532 strains of B2 phylogenetic group. According to the frequency of this clone in B2 commensal strains (18%), 14 and 96 would have been expected in the two collections, respectively.

Survival in Water

A human specific strain of *E. coli* could be a useful marker in microbial source tracking studies that attempt to determine if human faecal contamination of a water body is occurring. Consequently, we tested the survival of ED1a and compared it to the survival of *E. coli* K12 (Bogosian et al., 1996). In non-sterile river water at 20° C. the decline in viable cell counts of both strains are identical, and by day 9 neither strain can be detected (FIG. 2A). This result is in accordance with previously reported outcomes for K12 (Bogosian et al., 1996). In sterile river water at 20° C., viable cell counts of both strains declined by only 1 to 2 log in 35 days, with ED1a exhibiting poorer survival than K12 (FIG. 2B). These findings are consistent with earlier suggestions that the decline of *E. coli* populations in water is due to predation by protozoa, phages and exposure to heat-labile toxins.

Discussion

Host-specific *E. coli* pathogens are not unknown, for example it has long been thought that *Shigella* strains are primate specific (Donnenberg 2002) and there are rabbit specific enteropathogenic *E. coli* (Leyton et al., 2007). However, this is the first report of what is apparently a human-host specific commensal strain of *E. coli*. This clone belongs to the B2 phylogenetic group and, although B2 strains are often responsible for extra-intestinal infection (Picard et al., 1999), strains of this clone appear to rarely cause disease. The B2 VIII/O81 clone is absent from the Acthman *E. coli* MLST database and over half of the 1400 isolates in this database are listed as pathogens (Wirth et al., 2006). Based on its virulence determinant pattern and/or serotype, this clone is also absent from European and American collections of B2 strains responsible for newborn meningitis (n=99, Bonacorsi et al., 2003) and urosepsis (n=108, Bingen-Bidois et al., 2002; Johnson and Stell, 2000). Finally, none of the strains of this clone is virulent in the mouse model of extra-intestinal infection.

B2 VIII/O81 clone appears to be highly successful as it has been found on three continents and, in some populations, it can represent up to 7% of the isolates taken from human faeces. The reason for the absence of this clone in humans living in Australia is unknown. Geographic isolation is unlikely to be the answer, as over 60% of the MLST sequence types isolated from Australian humans have been detected in other parts of the world (unpublished data). All isolates of the B2 VIII clone with an O81 serotype are also very homogeneous in terms of the possessing a very similar suit of genes, that in other B2 strains have a highly polymorphic distribution and this observation is consistent with the idea that the clone has undergone a recent expansion.

The existence of a human-specific *E. coli* clone has immediate applied applications:

The B2 VIII/O81 clone can be used as a probiotic, as it appears to be avirulent and good coloniser of the human gut. The avirulent nature of this strain means that it might be particularly appropriate for use in highly vulnerable patients, such as those in intensive care, the immunocomprised, or premature infants. By comparison the currently used probiotic strains, Nissle O6 strain (Mutaflor®) isolated in 1917 from the faeces of a healthy soldier (Sun et al., 2005) and the A0 34/86 O83 strain isolated from porcine faeces (Hejnova, et al., 2005), are highly virulent in our mouse model of extra-intestinal virulence (killing 10 and 9 mice out of 10 inoculated, respectively).

Microbial source tracking is another application of the O81/B2 subgroup VIII clone. The usefulness of the microbial indicators as tool risk assessment can be significantly enhanced by the use of a human specific clone. The fact that all the individuals do not carry the O81/B2 subgroup VIII clone is not a problem as human faecal pollution is generally due to release of sewage from wastewater treatment plants or septic tanks, and therefore represents faecal contamination not by individuals but by populations. The absence of growth in water makes the B2 subgroup VIII/O81 clone a good marker of human faecal contamination of water. Furthermore, the PCR assay that we have developed can be used to identify the clone directly from water or soil samples.

CONCLUSIONS

*Escherichia coli* is a widespread commensal of the intestinal tract of humans and other vertebrates that occasionally causes intestinal and extra-intestinal diseases. Up to now, no strong association between a particular clone and a given host species has been found. By screening with a PCR based assay a panel of 723 commensal and clinical human as well as 904 faecal animal strains from four continents, we have identified a human specific clone of O81 serotype belonging to the B2 subgroup VIII as determined by multi-locus sequence typing. Members of this clone are widespread in Africa, Europe and America but not in Australia, almost always isolated in commensal conditions and increase in frequency during the past twenty years. They are able to achieve numerical dominance within a single host, are avirulent in a mouse model of extraintestinal virulence and survive but do not grow in water. They thus can be used as probiotic or for microbiological source tracking of water faecal contamination.

REFERENCES

Throughout this application, various references describe the state of the art to which this invention pertains. The disclosures of these references are hereby incorporated by reference into the present disclosure.

Barnes, B. and D. Gordon. 2004. Coliform dynamics and the implications for source tracking. Environ Microbiol 6: 501-509.

Bingen-Bidois, M., O. Clermont, S. Bonacorsi, M. Terki, N. Brahimi, C. Loukil, D. Barraud, and E. Bingen. 2002. Phylogenetic analysis and prevalence of urosepsis strains of *Escherichia coli* bearing pathogenicity island-like domains. Infect Immun 70: 3216-3236.

Blanco, J. E., M. Blanco, A. Mora, and J. Blanco. 1997. Production of toxins (enterotoxins, verotoxins, and necrotoxins) and colicins by *Escherichia coli* strains isolated from septicemic and healthy chickens: relationship with in vivo pathogenicity. J Clin Microbiol 35: 2953-2957.

Bogosian, G., L. E. Sammons, P. J. L. Morris, J. P. O'Neil, M. A. Heitkamp, and D. B. Weber. 1996. Death of the *Escherichia coli* K-12 strain W3110 in soil and water. Appl Environ Microbiol 62: 4114-4120.

Bonacorsi, S., O. Clermont, V. Houdouin, C. Corevant, N. Brahimi, A. Marecat, C. Tinsley, X. Nassif, M. Lange, and E. Bingen. 2003. Molecular analysis and experimental virulence of Fraench and North American *Escherichia coli* neonatal meningitis isolates: identification of a new virulent clone. J Infect Dis 187: 1895-1906.

Clermont, O., J. R. Johnson, M. Menard, and E. Denamur. 2007. Determination of *Escherichia coli* O types by allele-specific polymerase chain reaction: application to the O types involved in human septicemia. Diagn Microbiol Infect Dis 57: 129-156.

Donnenberg, M. 2002. *Escherichia coli* virulence mechanisms of versatile pathogen. Elsevier Science Ed ed, San Diego Calif.

Duriez, P., O. Clermont, S. Bonacorsi, E. Bingen, A. Chaventre, J. Elion, B. Picard, and E. Denamur. 2001. Commensal *Escherichia coli* isolates are phylogenetically distributed among geographically distinct human populations. Microbiology 147: 1671-1676.

Escobar-Páramo, P., O. Clermont, A. Blanc-Potard, D. Bui, C. Le Bouguenec, and E. Denamur. 2004a. A specific genetic background is required for acquisition and expression of virulence factors in *Escherichia coli*. Mol Biol Evol 21: 1085-1094.

Escobar-Páramo, P., K. Grenet, A. Le Menach, L. Rode, E. Salgado, C. Amorin, S. Gouriou, B. Picard, M. Cherif Rahimy, A. Andremont, E. Denamur, and R. Ruimy. 2004b. Large-scale population structure of human commensal *Escherichia coli* isolates. Appl Environ Microbiol 70: 5698-5700.

Escobar-Páramo, P., A. Sabbagh, P. Darlu, O. Pradillon, C. Vaury, E. Denamur, and G. Lecointre. 2004c. Decreasing the effects of horizontal gene transfer on bacterial phylogeny: the *Escherichia coli* case study. Mol Phyl Evol 30: 243-250.

Escobar-Páramo, P., A. Le Menac'h, T. Le Gall, C. Amorin, S. Gouriou, B. Picard, D. Skurnik, and E. Denamur. 2006. Identification of forces shaping the commensal *Escherichia coli* genetic structure by comparing animal and human isolates. Environ Microbiol 8: 1975-1984.

Gerdes, S. Y., M. D. Scholle, J. W. Campbell, G. Balazsi, E. Ravasz, M. D. Daugherty, A. L. Somera, N. C. Kyrpides, I. Anderson, M. S. Gelfand, A. Bhattacharya, V. Kapatral, M. D'Souza, M. V. Baev. Y. Grechkin, F. Mseeh, M. Y. Fonstein, R. Overbeek, A. L. Barabasi, Z. N. Oltvai, and A. L. Osterman. 2003. Experimental determination and system level analysis of essential genes in *Escherichia coli* MG1655. J Bacteriol 185: 5673-5684.

Gordon, D. M. 2001. Geographical structure and host specificity in bacteria and the implications for tracing the source of coliform contamination. Microbiology 147: 1079-85.

Gordon, D. M., and A. Cowling. 2003. The distribution and genetic structure of *Escherichia coli* in Australian vertebrates: host and geographic effects. Microbiology 149: 3575-3586.

Gordon, D. M., S. E. Stern, and P. J. Collignon. 2005. Influence of the age and sex of human hosts on the distribution of *Escherichia coli* ECOR groups and virulence traits. Microbiology 151: 15-23.

Gordon, D. M., and C. L. O'Brien. 2006. Bacteriocin diversity and the frequency of multiple bacteriocin production in *Escherichia coli*. Microbiology 152: 3239-44.

Harms, H., Wells M. C., and van der Meer J. R. 2006. Whole-cell living biosensors—are they ready for environmental application? Appl Microbiol Biotechnol 70: 273-280.

Hejnova, J., U. Dobrindt. R. Nemcova, C. Rusniok, A. Bomba, L. Frangeul, J. Hacker, P. Sebo, and C. Buchrieser. 2005. Characterization of the flexible genome complement of the commensal *Escherichia coli* strain A0 34/86 (O83: K24: H31). Microbiology 151: 385-398.

Herzer, P. J., S. Inouye, M. Inouye, and T. S. Whittam. 1990. Phylogenetic distribution of branched RNA-linked multicopy single-stranded DNA among natural isolates of *Escherichia coli*. J Bacteriol 172: 6175-6181.

Jauréguy, E. Carbonnelle, S. Bonacorsi, C. Clec'h, P. Casassus, E. Bingen, B. Picard, X. Nassif, O. Lortholary, 2007. Host and bacterial determinants of initial severity and outcome of *Escherichia coli* sepsis. Clinical Microbiology and Infection, 13: 854-862.

Johnson, J. R., and A. L. Stell. 2000. Extended virulence genotypes of *Escherichia coli* strains from patients with urosepsis in relation to phylogeny and host compromise. J Infect Dis 181: 261-272.

Johnson, J. R., O. Clermont, M. Menard, M. A. Kuskowski, B. Picard, and E. Denamur. 2006. Experimental mouse lethality of *Escherichia coli* isolates, in relation to accessory traits, phylogenetic group, and ecological source. J Infect Dis 194: 141-1150.

Karlin and Altschul 1990. Methods for assessing the statistical significance of molecular sequence features by using general scoring schemes. Proc. Natl. Acad. Sci. USA 87: 2264).

Karlin and Altschul 1993. Applications and statistics for multiple high-scoring segments in molecular sequences. Proc. Natl. Acad. Sci. USA 90: 5873-5877.

Leyton, D. L., L. M. Adams, M. Kelly, J. Sloan, M. Tauschek, R. M. Robins-Browne, and E. L. Hartland. 2007 Contribution of a novel gene rpeA encoding a putative autotransporter adhesin to intestinal colonization by rabbit enteropathogenic *Escherichia coli*. Infect Immun doi: 10.1128/IAI.00972-06

Myers and Miller, 1988. Optimal alignments in linear space. Comput Appl Biosci 4: 11-17.

Nataro and Kaper, 1998. Diarrheagenic *Escherichia coli*. Clin. Microbiol. Rev. 1998 11: 142-201

Needleman and Wunsch 1970. A general method applicable to the search for similarities in the amino acid sequence of two proteins. J. Mol. Biol. 48: 443-453.

Ochman, H. and R. K. Selander. 1984. Standard reference strains of *Escherichia coli* from natural populations. J Bacteriol 157: 690-693.

Pearson and Lipman 1988. Improved tools for biological sequence comparison. Proc. Natl. Acad. ScL 85: 2444-2448.

Picard, B., J. Garcia, S. Gouriou, P. Duriez, N. Brahimi, E. Bingen, J. Elion, and E. Denamur 1999. The link between phylogeny and virulence in *Escherichia coli* extraintestinal infection. Infect Immun 67: 546-553.

Power M L, Littlefield-Wyer J, Gordon D M, Veal D A, Slade M B. 2005. Phenotypic and genotypic characterization of encapsulated *Escherichia coli* isolated from blooms in two Australian lakes. Environ Microbiol. 7 (5): 631-40.

Scott, T. M., J. B. Rose, T. M. Jenkins, S. R. Farrah, and J. Lukasik. 2002. Microbial source tracking: current methodology and future directions. Appl Environ Microbiol 68: 5796-5803.

Smith et al. 1981. Comparative biosequence metrics. Adv. Appl. Math. 2: 482.

Souza V, M. Rocha, A. Valera, and L. E. Eguiarte. 1999. Genetic structure of natural populations of *Escherichia coli* in wild hosts on different continents. Appl Environ Microbiol 65: 3373-3385.

Sun, J., F. Gunzer, A. M. Westendorf, J. Buer, M. Scharfe, M. Jarek, F. Gössling, H. Blöcker, and A. P. Zeng. 2005. Genomic peculiarity of coding sequences and metabolic potential of probiotic *Escherichia coli* strain Nissle 1917 inferred from raw genome data. J Biothechnol 117: 147-161.

Vassaux, G., J. Nitcheu, S. Jezzard, and N. R. Lemoine. 2006. Bacterial gene therapy strategies. J Pathol 208: 290-8.

Wirth, T., D. Falush, R. Lan, F. Colles, P. Mensa, L. H. Wieler, H. Karch, P. R. Reeves, M. C. Maiden, H. Ochman, and M. Achtman. 2006. Sex and virulence in *Escherichia coli*: an evolutionary perspective. Mol Microbiol 60: 1136-1151.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08178340B2). An electronic copy of the "Sequence Listing" will also be available from the USPTO upon request and payment of the fee set forth in 37 CFR 1.19(b)(3).

The invention claimed is:

1. A strain of *Escherichia coli* deposited at the COLLECTION NATIONALE DE CULTURES DE MICROORGANISMES (CNCM) under accession number CNCM I-3734.

2. An enteric-coated formulation comprising a lyophilized strain according to claim 1.

3. A strain according to claim 1, wherein said strain is genetically modified and contains one or more heterologous nucleotide sequences.

4. A strain according to claim 1, wherein said strain is genetically modified in order to express a reporter protein.

* * * * *